(12) United States Patent
Lesinski et al.

(10) Patent No.: US 8,876,689 B2
(45) Date of Patent: *Nov. 4, 2014

(54) HEARING AID MICROACTUATOR

(75) Inventors: S. George Lesinski, Cincinnati, OH (US); Armand P. Neukermans, Portola Valley, CA (US)

(73) Assignee: OtoKinetics Inc., Salt Lake City, UT (US)

( * ) Notice: Subject to any disclaimer, the term of this patent is extended or adjusted under 35 U.S.C. 154(b) by 65 days.

This patent is subject to a terminal disclaimer.

(21) Appl. No.: 13/437,896

(22) Filed: Apr. 2, 2012

(65) Prior Publication Data

US 2012/0190914 A1   Jul. 26, 2012

Related U.S. Application Data

(63) Continuation of application No. 10/494,345, filed as application No. PCT/US02/34360 on Oct. 26, 2002, now Pat. No. 8,147,544.

(60) Provisional application No. 60/335,944, filed on Oct. 30, 2001, provisional application No. 60/409,514, filed on Sep. 10, 2002.

(51) Int. Cl.
  *H04R 25/00* (2006.01)
  *A61N 1/05* (2006.01)
  *A61B 17/16* (2006.01)
  *A61N 1/36* (2006.01)

(52) U.S. Cl.
  CPC .......... *A61B 17/1679* (2013.01); *A61N 1/0541* (2013.01); *A61N 1/36032* (2013.01)
  USPC .......................................................... 600/25

(58) Field of Classification Search
  USPC ............ 606/73, 180; 600/372, 373, 375, 379, 600/383, 386; 381/324, 328, 329, 331
  See application file for complete search history.

(56) References Cited

U.S. PATENT DOCUMENTS 622,328 A   4/1899 Collins
1,076,210 A   10/1913 Kerr (Continued)

FOREIGN PATENT DOCUMENTS

CA   2 246 281 C   8/1997
CA   2 250 410 C   10/1997

(Continued)

OTHER PUBLICATIONS

Bekesy, "Cochlear Mechanics. The Pattern of Vibrations in the Cochlea," Experiments in Hearing Part 4 pp. 403-484 (1960).

(Continued)

*Primary Examiner* — Christopher Beccia
(74) *Attorney, Agent, or Firm* — Nixon Peabody LLP

(57) ABSTRACT

A fenestration piercing the otic capsule bone of the cochlea receives a therapeutic appliance, such as a microactuator, plug, micropump for drug or therapeutic agent delivery, electrode, and the like. Several different ways of achieving a 'water tight' seal between the otic capsule bone and the therapeutic appliance are provided. The therapeutic appliance may be implanted with or without a sheath or sleeve lining the wall of the fenestration formed using specialized surgical burrs. The burrs permit safely fenestrating the otic capsule bone adjacent to the scala tympani of the cochlea without damaging the basilar membrane or organ of corti. This approach may also be adopted for safely fenestrating other areas of the inner ear such as the scala vestibuli, bony labyrinth of semicircular canals, or walls of the vestibule, or the oval or round windows thereof.

8 Claims, 9 Drawing Sheets

(56) References Cited

U.S. PATENT DOCUMENTS

| | | |
|---|---|---|
| 1,200,921 A | 10/1916 | Chester |
| 2,702,354 A | 2/1955 | Chorpening |
| 2,901,551 A | 8/1959 | Passow |
| 2,978,846 A | 4/1961 | Barron |
| 3,125,646 A | 3/1964 | Lewis |
| 3,170,046 A | 2/1965 | Leale |
| 3,209,081 A | 9/1965 | Ducote et al. |
| 3,227,836 A | 1/1966 | Renwick, Sr. |
| 3,304,446 A | 2/1967 | Martinek et al. |
| 3,346,704 A | 10/1967 | Mahoney |
| 3,557,775 A | 1/1971 | Mahoney |
| 3,594,514 A | 7/1971 | Wingrove |
| 3,633,217 A | 1/1972 | Lance |
| 3,674,945 A | 7/1972 | Hands |
| 3,676,611 A | 7/1972 | Stephens |
| 3,712,962 A | 1/1973 | Epley |
| 3,763,333 A | 10/1973 | Lichowsky |
| 3,764,748 A | 10/1973 | Branch et al. |
| 3,771,173 A | 11/1973 | Lamb, Jr. |
| 3,842,440 A | 10/1974 | Karlson |
| 3,870,832 A | 3/1975 | Fredrickson |
| 3,882,285 A | 5/1975 | Nunley et al. |
| 3,894,339 A | 7/1975 | Manzi |
| 3,919,722 A | 11/1975 | Harmison |
| 3,947,825 A | 3/1976 | Cassada |
| 4,063,048 A | 12/1977 | Kissiah, Jr. |
| 4,069,400 A | 1/1978 | Johanson et al. |
| 4,071,029 A | 1/1978 | Richmond et al. |
| 4,078,160 A | 3/1978 | Bost |
| 4,133,984 A | 1/1979 | Akiyama |
| 4,143,661 A | 3/1979 | LaForge et al. |
| 4,150,262 A | 4/1979 | Ono |
| 4,213,207 A | 7/1980 | Wilson |
| 4,251,686 A | 2/1981 | Sokolich |
| 4,284,856 A | 8/1981 | Hochmair et al. |
| 4,342,936 A | 8/1982 | Marcus et al. |
| RE31,031 E | 9/1982 | Kissiah, Jr. |
| 4,352,960 A | 10/1982 | Dormer et al. |
| 4,357,497 A | 11/1982 | Hochmair et al. |
| 4,367,426 A | 1/1983 | Kumada et al. |
| 4,369,530 A | 1/1983 | Robinson et al. |
| 4,383,196 A | 5/1983 | Perduijn et al. |
| 4,419,995 A | 12/1983 | Hochmair et al. |
| 4,428,377 A | 1/1984 | Zollner et al. |
| 4,441,210 A | 4/1984 | Hochmair et al. |
| 4,498,461 A | 2/1985 | Hakansson |
| 4,524,247 A | 6/1985 | Lindenberger et al. |
| 4,533,795 A | 8/1985 | Baumhauer, Jr. et al. |
| 4,558,184 A | 12/1985 | Busch-Vishniac et al. |
| 4,592,370 A | 6/1986 | Lee et al. |
| 4,606,329 A | 8/1986 | Hough |
| 4,611,598 A | 9/1986 | Hortmann et al. |
| 4,617,913 A | 10/1986 | Eddington |
| 4,655,776 A | 4/1987 | Lesinski |
| 4,662,358 A | 5/1987 | Farrar et al. |
| 4,665,896 A | 5/1987 | LaForge et al. |
| 4,666,443 A | 5/1987 | Portner |
| 4,712,244 A | 12/1987 | Zwicker et al. |
| 4,726,099 A | 2/1988 | Card et al. |
| 4,729,366 A | 3/1988 | Schaefer |
| 4,751,738 A | 6/1988 | Widrow et al. |
| 4,756,312 A | 7/1988 | Epley |
| 4,773,095 A | 9/1988 | Zwicker et al. |
| 4,793,825 A | 12/1988 | Benjamin et al. |
| 4,817,607 A | 4/1989 | Tatge |
| 4,817,609 A | 4/1989 | Perkins et al. |
| 4,844,080 A | 7/1989 | Frass et al. |
| 4,850,962 A | 7/1989 | Schaefer |
| 4,892,108 A * | 1/1990 | Miller et al. .................. 607/116 |
| 4,904,078 A | 2/1990 | Gorike |
| 4,908,509 A | 3/1990 | Senturia |
| 4,928,264 A | 5/1990 | Kahn |
| 4,932,405 A | 6/1990 | Peeters et al. |
| 4,943,750 A | 7/1990 | Howe et al. |
| 4,956,867 A | 9/1990 | Zurek et al. |
| 4,957,478 A | 9/1990 | Maniglia |
| 4,985,926 A | 1/1991 | Foster |
| 4,988,333 A | 1/1991 | Engebretson et al. |
| 4,999,819 A | 3/1991 | Newnham et al. |
| 5,015,224 A | 5/1991 | Maniglia |
| 5,015,225 A | 5/1991 | Hough et al. |
| 5,033,999 A | 7/1991 | Mersky |
| 5,061,282 A | 10/1991 | Jacobs |
| 5,070,535 A | 12/1991 | Hochmair et al. |
| 5,085,628 A | 2/1992 | Engebretson et al. |
| 5,091,820 A | 2/1992 | Iwaya et al. |
| 5,095,904 A | 3/1992 | Seligman et al. |
| 5,176,620 A | 1/1993 | Gilman |
| 5,180,391 A | 1/1993 | Beoni |
| 5,191,559 A | 3/1993 | Kahn et al. |
| 5,239,588 A | 8/1993 | Davis |
| 5,271,397 A | 12/1993 | Seligman et al. |
| 5,272,283 A | 12/1993 | Kuzma |
| 5,276,657 A | 1/1994 | Newnham et al. |
| 5,276,739 A | 1/1994 | Krokstad et al. |
| 5,277,694 A | 1/1994 | Leysieffer et al. |
| 5,282,858 A | 2/1994 | Bisch et al. |
| 5,306,299 A | 4/1994 | Applebaum |
| 5,318,502 A | 6/1994 | Gilman |
| 5,338,287 A | 8/1994 | Miller et al. |
| 5,344,387 A | 9/1994 | Lupin |
| 5,350,966 A | 9/1994 | Culp |
| 5,376,857 A | 12/1994 | Takeuchi et al. |
| 5,388,163 A | 2/1995 | Elko et al. |
| 5,408,534 A | 4/1995 | Lenzini et al. |
| 5,411,467 A | 5/1995 | Hortmann et al. |
| 5,456,654 A | 10/1995 | Ball |
| 5,471,721 A | 12/1995 | Haertling |
| 5,478,093 A | 12/1995 | Eibl et al. |
| 5,481,152 A | 1/1996 | Buschulte |
| 5,483,599 A | 1/1996 | Zagorski |
| 5,489,226 A | 2/1996 | Nakamura et al. |
| 5,490,034 A | 2/1996 | Zavracky et al. |
| 5,490,220 A | 2/1996 | Leoppert |
| 5,493,470 A | 2/1996 | Zavracky et al. |
| 5,498,226 A | 3/1996 | Lenkauskas |
| 5,517,154 A | 5/1996 | Baker et al. |
| 5,554,096 A | 9/1996 | Ball |
| 5,558,618 A | 9/1996 | Maniglia |
| 5,564,479 A | 10/1996 | Yoshihara |
| 5,601,125 A | 2/1997 | Parsoneault et al. |
| 5,632,841 A | 5/1997 | Hellbaum et al. |
| 5,677,965 A | 10/1997 | Moret et al. |
| 5,722,989 A | 3/1998 | Fitch et al. |
| 5,737,430 A | 4/1998 | Widrow |
| 5,772,575 A | 6/1998 | Lesinski et al. |
| 5,796,188 A | 8/1998 | Bays |
| 5,833,626 A | 11/1998 | Leysieffer |
| 5,881,158 A | 3/1999 | Lesinski et al. |
| 5,897,486 A | 4/1999 | Ball et al. |
| 5,906,635 A | 5/1999 | Maniglia |
| 5,949,895 A | 9/1999 | Ball et al. |
| 5,951,301 A | 9/1999 | Younker |
| 5,951,601 A | 9/1999 | Lesinski et al. |
| 5,977,689 A * | 11/1999 | Neukermans .................. 310/324 |
| 5,984,859 A | 11/1999 | Lesinski |
| 6,053,920 A * | 4/2000 | Carlsson et al. .............. 606/304 |
| 6,082,199 A | 7/2000 | Frick et al. |
| 6,093,144 A | 7/2000 | Jaeger et al. |
| 6,101,258 A | 8/2000 | Killion et al. |
| 6,199,600 B1 | 3/2001 | Ahn et al. |
| 6,381,336 B1 | 4/2002 | Lesinski et al. |
| 6,440,102 B1 * | 8/2002 | Arenberg et al. .......... 604/96.01 |
| 6,561,231 B2 * | 5/2003 | Neukermans ..................... 141/4 |
| 6,599,297 B1 | 7/2003 | Carlsson et al. |
| 6,628,991 B2 | 9/2003 | Kuzma et al. |
| 7,409,070 B2 | 8/2008 | Pitulia |
| 7,618,450 B2 | 11/2009 | Zarowski et al. |

(56) References Cited

U.S. PATENT DOCUMENTS

| | | | |
|---|---|---|---|
| 8,147,544 B2 * | 4/2012 | Lesinski et al. ................ | 623/10 |
| 2008/0215148 A1 | 9/2008 | Lesinski et al. | |

FOREIGN PATENT DOCUMENTS

| | | |
|---|---|---|
| CA | 2 256 389 C | 11/1997 |
| CA | 2 479 822 A1 | 11/1997 |
| CA | 2 261 004 C | 1/1998 |
| DE | 28 25 233 A1 | 1/1979 |
| DE | 36 05 915 A1 | 8/1987 |
| EP | 0 222 509 A2 | 5/1987 |
| EP | 0 242 038 A2 | 10/1987 |
| EP | 0 263 254 A1 | 4/1988 |
| EP | 0 341 902 A2 | 11/1989 |
| EP | 0 563 767 A1 | 10/1993 |
| FR | 2 688 132 A1 | 9/1993 |
| GB | 2 176 078 A | 12/1986 |
| GB | 2 188 290 A | 9/1987 |
| JP | 51126774 U | 10/1976 |
| JP | 55044239 A | 3/1980 |
| JP | 58089260 A | 5/1983 |
| JP | 58089860 U | 6/1983 |
| JP | 58147400 U | 10/1983 |
| JP | 4070100 A | 3/1992 |
| WO | WO 82/01655 A1 | 5/1982 |
| WO | WO 90/00040 A1 | 1/1990 |
| WO | WO 90/07915 A1 | 7/1990 |
| WO | WO 94/17645 A1 | 8/1994 |

OTHER PUBLICATIONS

Carver, "Hearing Aids: A Historical and Technical Review," Handbook of Clinical Audiology, Section VII pp. 564-576 (1972).

Epley, "History of Implantable Hearing Aid Development: Review and Analysis," Surgery of the Inner Ear pp. 501-511 (1991).

Goode, "Current Status of Electromagnetic Implantable Hearing Aids," Otolaryngologic Clinics of North America 22 (1):201-9 (1969).

Killion, "The K-Amp Hearing Aid: An Attempt to Present High Fidelity for Persons with Impaired Hearing," American Journal of Audiology 2(2):52-74 (1993).

Lesinski et al., "CO2 Laser for Ostosclerosis: Safe Energy Parameters," Lasers for Otosclerosis 99(6, Part 2):9-12 (1989).

Lesinski et al., "CO2 Laser Stapedotomy," Lasers for Otosclerosis Laryngoscope 99(6, Part 2):20-4 (1989).

Lesinski et al., "Lasers for Otosclerosis: CO2 vs. Argon and KTP-532," Lasers for Otosclerosis Laryngoscope 99(6, Part 2):1-8 (1989).

Lesinski et al., "Lasers in Revision Stapes Surgery," Operative Techniques in Otolaryngology—Head and Neck Surgery 3(1):21-31 (1992).

Lesinski et al., "Stapedectomy Revision with the CO2 Laser," Lasers for Otosclerosis Laryngoscope 99(6, Part 2):13-9 (1989).

Lesinski, "Homograft (Allograft) Tympanoplasty Update," Laryngoscope 96(11):1211-20(1986).

Lesinski, "Homograft Tympanoplasty in Perspective. A Long-Term Clinical-Histologic Study of Formalin-Fixed tympanic Membranes Used for the Reconstruction of 125 Severely Damaged Middle Ears," Laryngoscope Supplement No. 32 93(11, Part 2):1-37 (1983).

Lesinski, "Lasers for Otosclerosis Which One if Any and Why," Lasers in Surgery and Medicine 10:448-57 (1990).

Lesinski, "Reconstruction of Hearing When Malleus is Absent: Torp vs. Homograft TMMI," Laryngoscope 94 (11):1443-6 (1984).

Maniglia, "Implantable Hearing Devices. State of the Art," Otolaryngologic Clinics of North America 22(1):175-200 (1989).

Nasa, "Thunder," national Aeronautics and Space Administration, Langley Research Center, Hampton, VA USA (1996).

Plester et al., "'How I Do It'—Otology and Neurotology. A Specific Issue and Its Solution. The Promotional Window Technique," Laryngoscope 93(6):824-5 (1983).

Wise et al., "Microfabrication Techniques for Integrated Sensors and Microsystems," Science 254:1335-42 (1991).

Yam, "Trends in Materials Science . Plastics Get Wired," Scientific American pp. 83-86 (1995).

Yanagihara et al., "Implantable Hearing Aid," Arch Otolaryngol Head Neck Surg 113:869-2 (1987).

International Search Report in PCT Application No. PCT/US2002/034360, mailed Apr. 15, 2003.

* cited by examiner

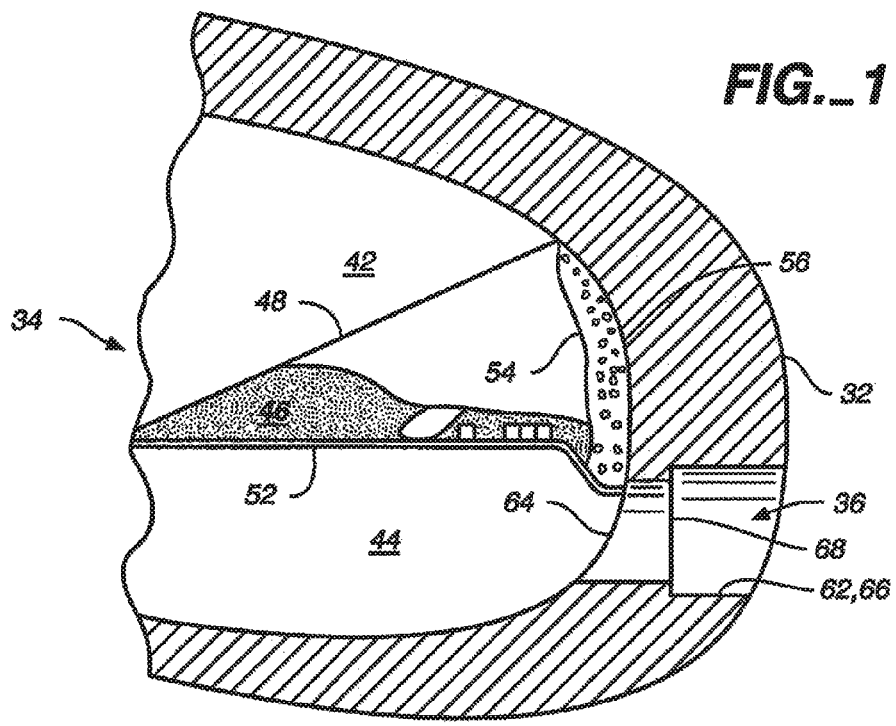
FIG._1
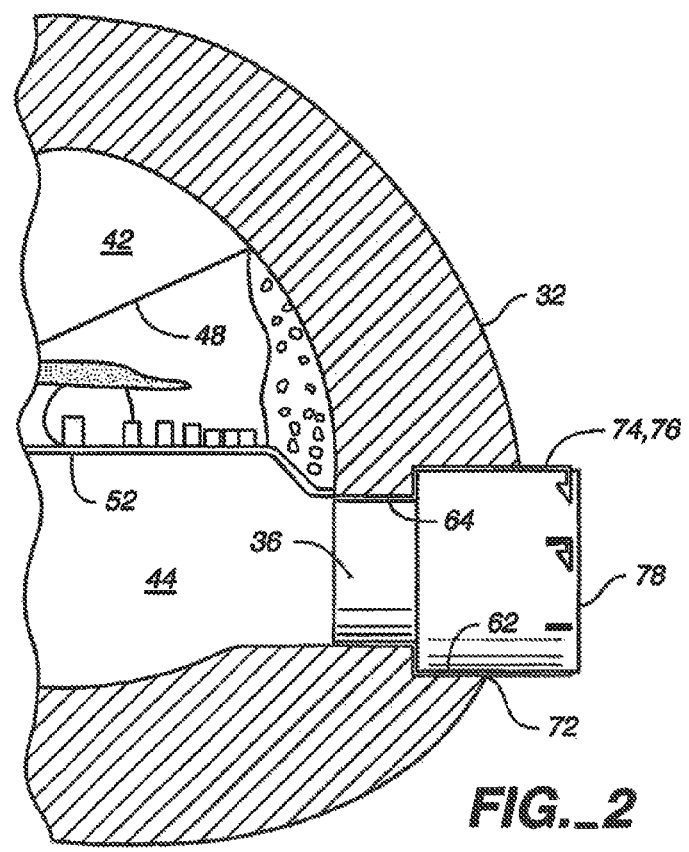
FIG._2

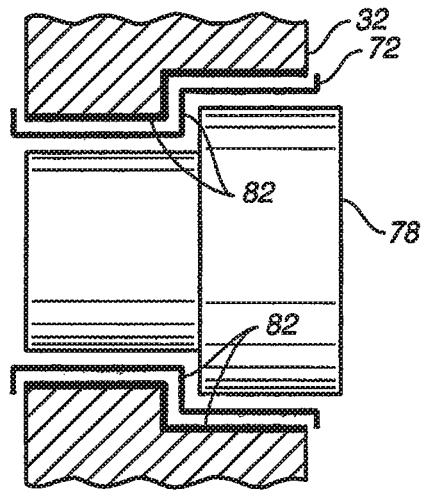
FIG._3
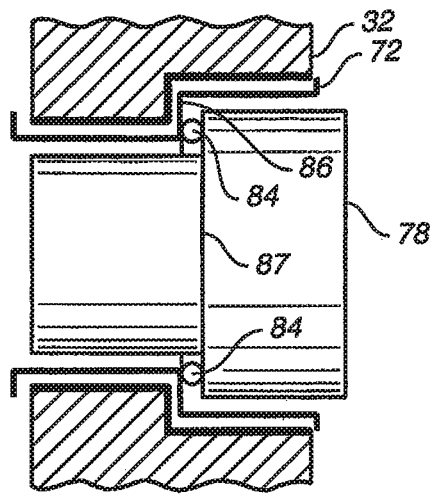
FIG._4
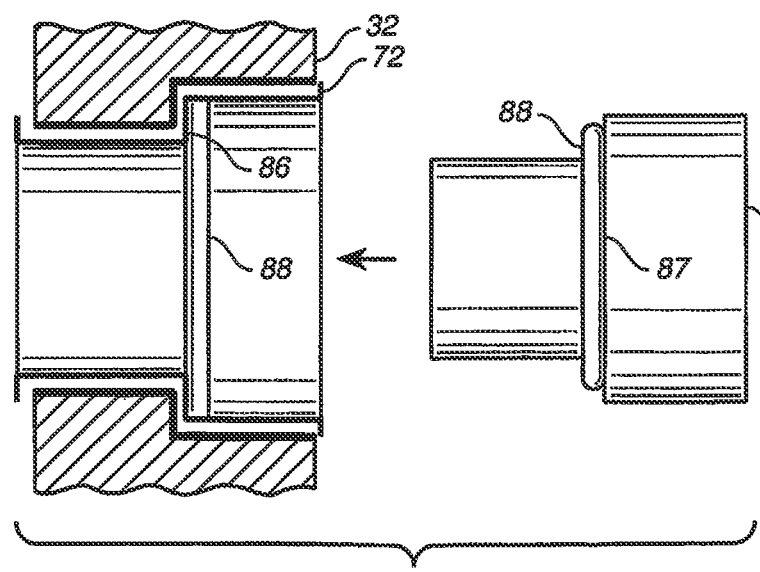
FIG._5

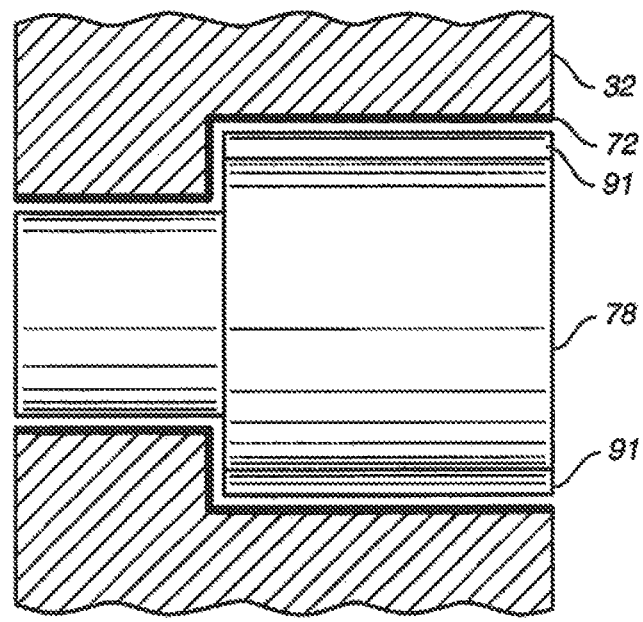
FIG._6
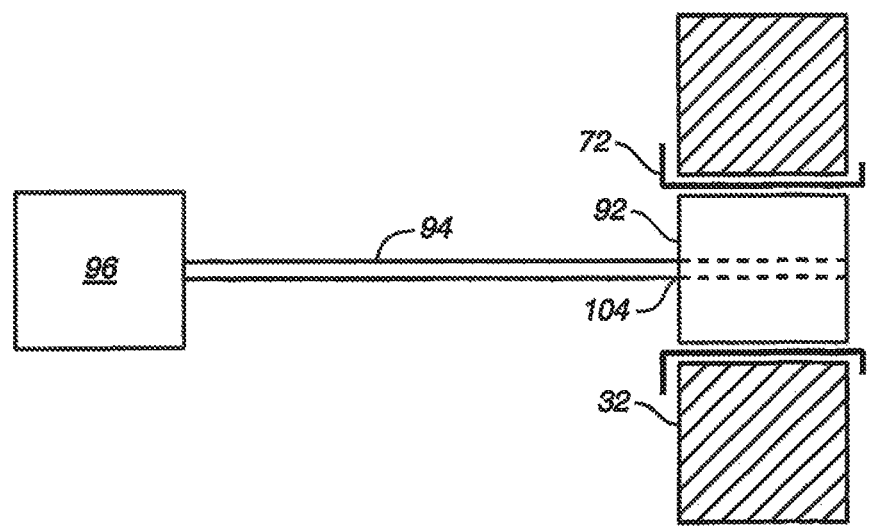
FIG._7

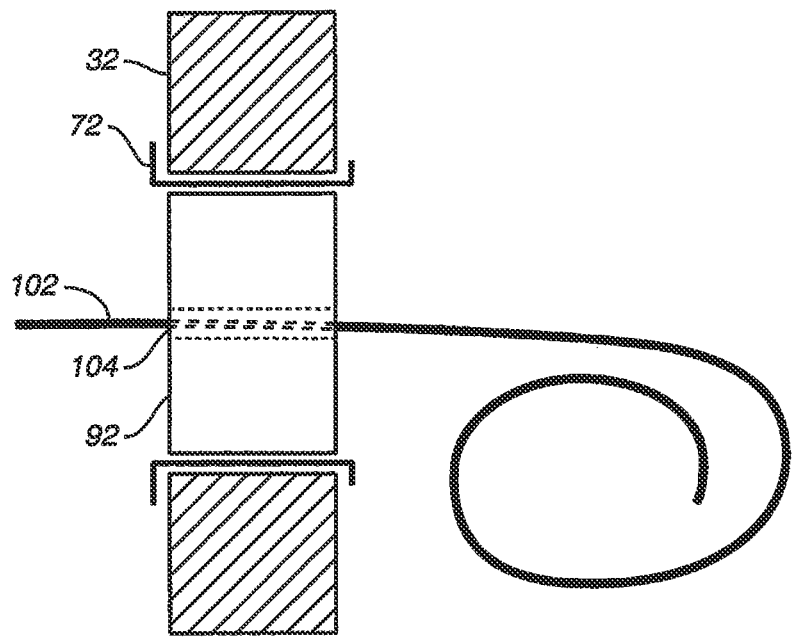
FIG._8
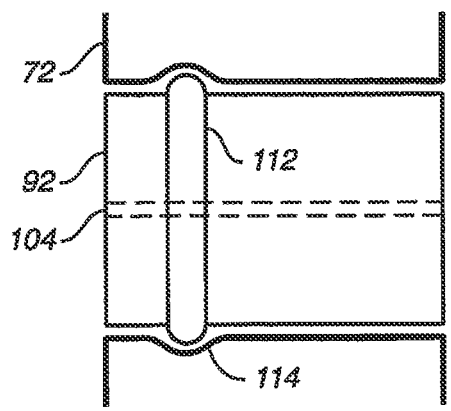
FIG._9

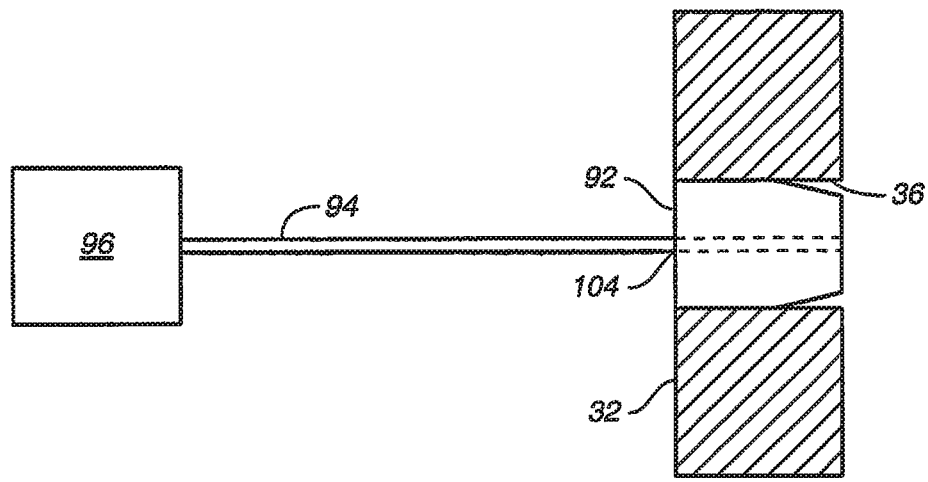
FIG._10
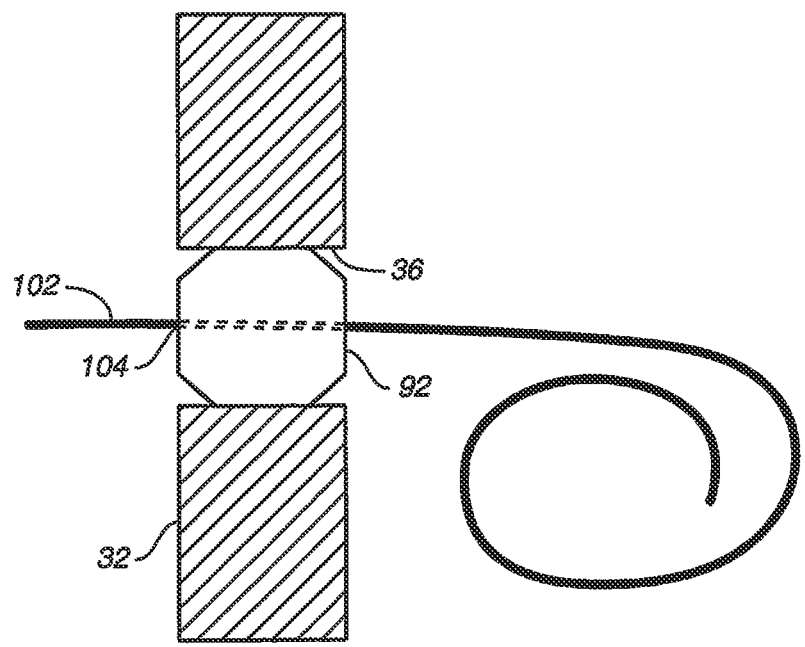
FIG._11

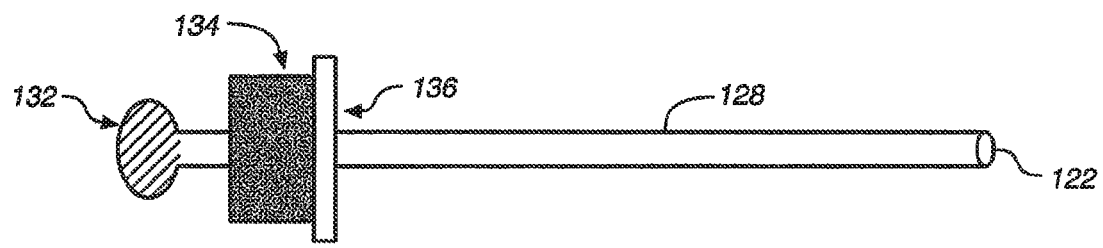
FIG._12a
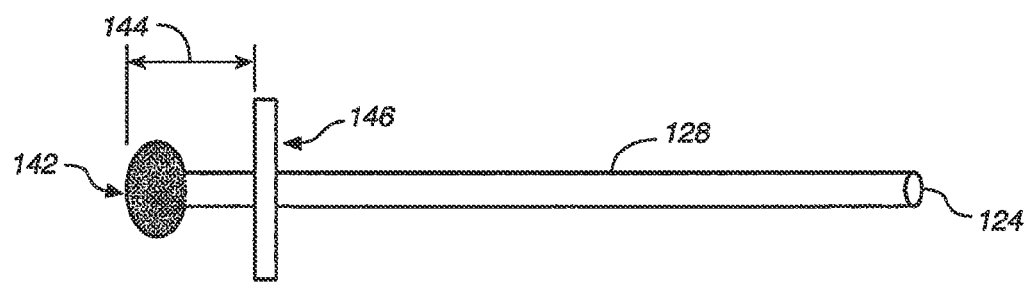
FIG._12b

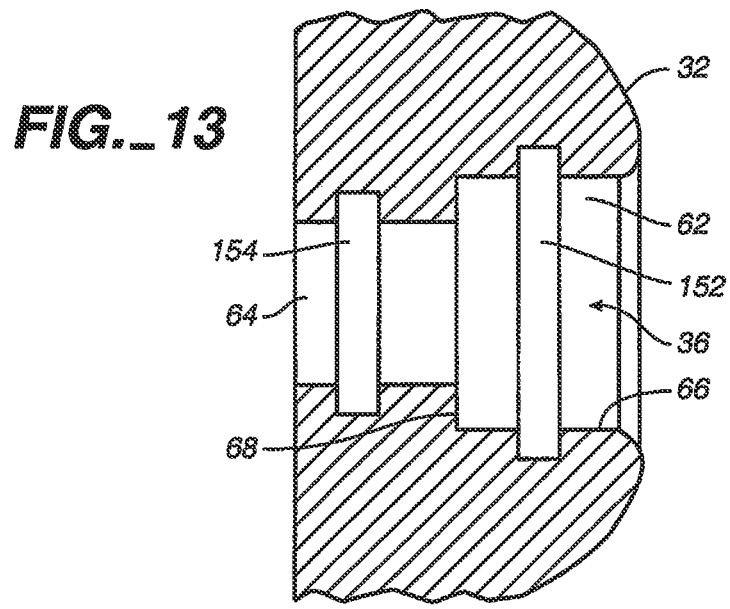
FIG._13
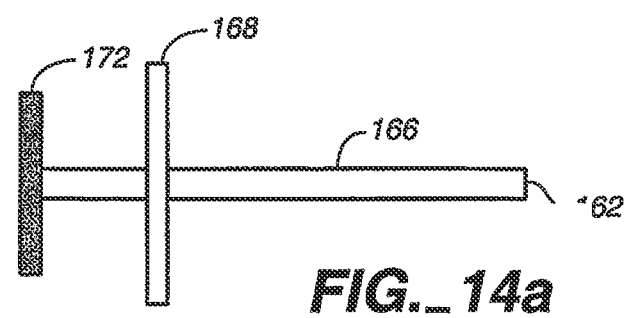
FIG._14a
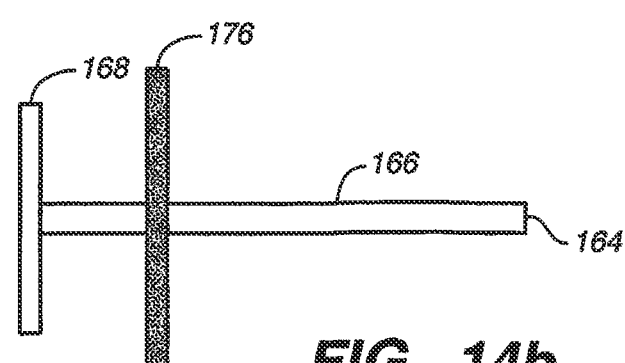
FIG._14b

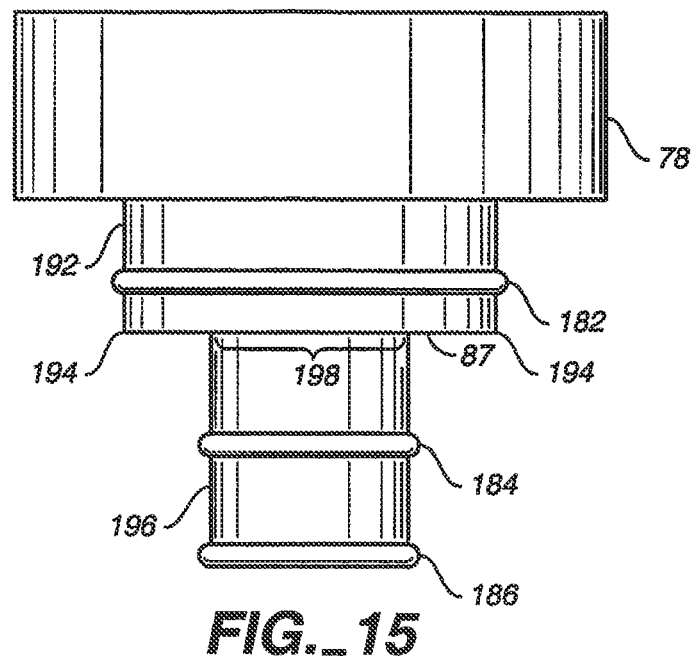
FIG._15
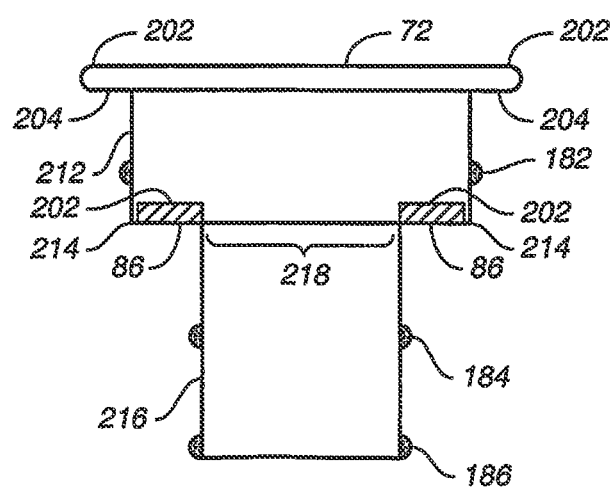
FIG._16

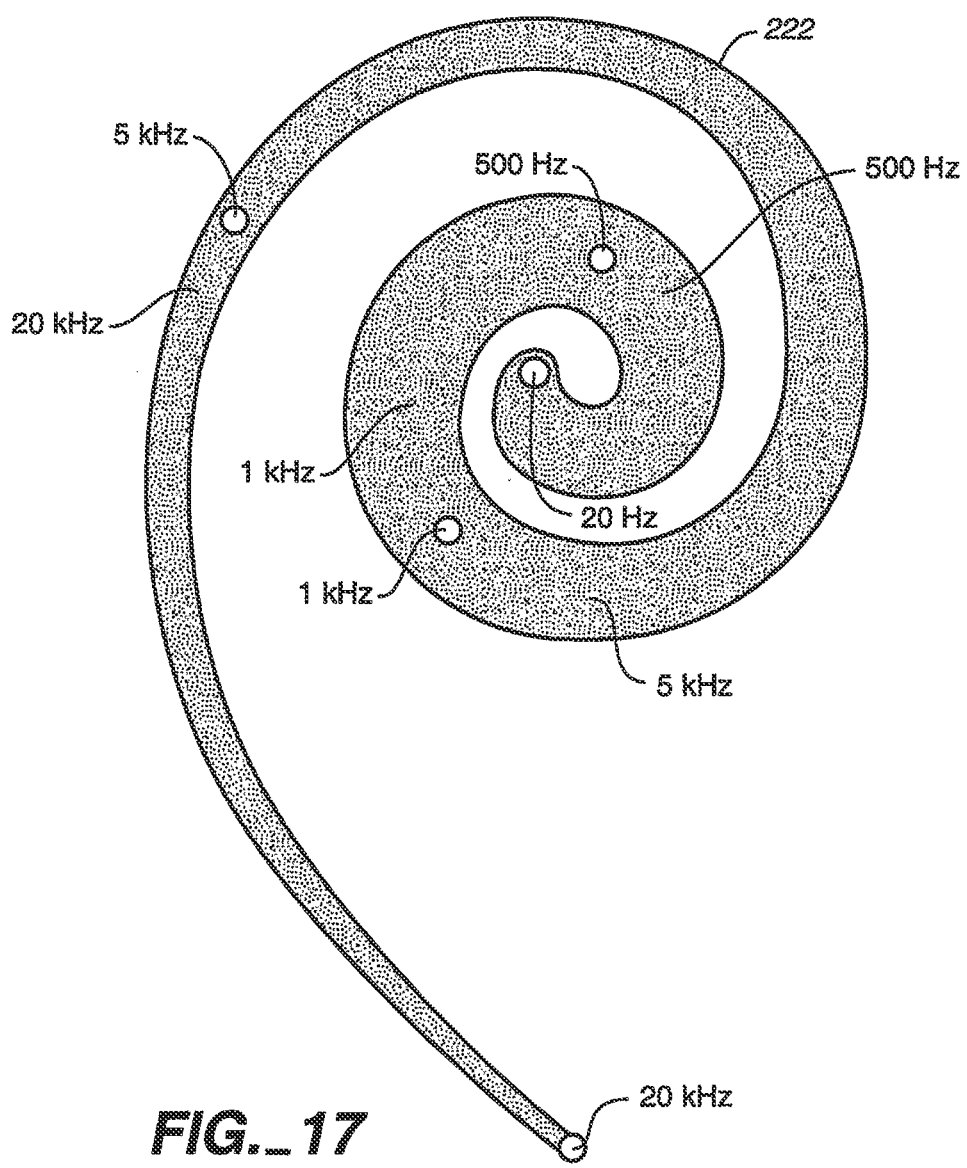
FIG._17

HEARING AID MICROACTUATOR

CROSS-REFERENCE TO RELATED APPLICATIONS

The present application is a continuation of co-pending U.S. patent application Ser. No. 10/494,345 filed Apr. 29, 2004, which is a National Phase of International Application No. PCT/US02/34360 filed Oct. 26, 2002 which claims benefit of U.S. Provisional Patent Application Ser. No. 60/335,944 filed Oct. 30, 2001 and U.S. Provisional Patent Application No. 60/409,514 filed Sep. 10, 2002 which are commonly owned herewith.

TECHNICAL FIELD

The present invention relates to a fully implantable hearing aid system, and more particularly to devices and methods for mounting a microactuator, or other therapeutic device, into a fenestration that pierces the wall of the cochlea of a patient.

BACKGROUND ART

A biologically sealed attachment into the wall of the cochlea of a patient that is stable and watertight is often desired, not only for an acoustic actuator, but also for various other medical devices. U.S. Pat. No. 5,951,601 ("the '601 patent") describes several methods for attaching a microactuator to a fenestration through the wall of the cochlea.

The invention disclosed in the '601 patent has several advantages. A casing locates the hearing device very securely, without vibration. In addition, the invention makes the removal of the hearing device easy, should this be required. Thirdly, together with a precise atraumatic fenestration procedure it provides for a very precise microactuator location, thereby ensuring that the microactuator is optimally situated in the cochlea, without damage to the delicate structures of the inner ear.

Specifically, the casing disclosed in the '601 patent receives a microactuator of an implantable hearing aid system. The casing is implanted into a fenestration that pierces the promontory of the otic capsule bone. The promontory is a projection of the cochlea which is a fluid-filled hearing portion of the inner ear. As described in the '601 patent, the casing is adapted for receiving and attaching to the subject either a microactuator included in the implantable hearing aid system, or a dummy plug to replace the microactuator should removal of the microactuator become necessary. Upon application of an electric signal to the microactuator, the microactuator directly stimulates fluid within the inner ear, which stimulation the subject perceives as sound.

A casing for attaching a microactuator of an implantable hearing aid system to a fenestration formed through a subject's promontory in accordance with the disclosure of the '601 patent includes a sleeve that has an outer surface. During implantation of the casing, a first end of the sleeve is received into the fenestration. Disposed in that location, the outer surface of the sleeve mates with the fenestration for securing the casing within the fenestration. The hollow sleeve includes an inner surface adapted to receive a barrel of the microactuator.

The casing also includes a flange that is integral with the sleeve. The flange projects outward from the outer surface of the sleeve about a second end of the sleeve that is located distal from the first end. The flange, through contact either with a mucosa that covers the promontory or with the promontory itself, limits a depth to which the first end of the sleeve may enter into the fenestration.

A casing in accordance with the '601 patent may employ various means for securing the sleeve within the fenestration such as screwing into the promontory or clamping to the promontory. Similarly, such a casing may fasten the microactuator to the casing in various ways such as by a threaded attachment, with screws, with button-and-socket snap fasteners, or with a slotted tongue-and-groove lock. A casing in accordance with the '601 patent may also include a keyway that receives a mating key formed on the barrel of the microactuator for establishing an orientation of the implanted microactuator.

One difficulty in a process for securing a therapeutic appliance into the wall of the cochlea is that the attachment be biologically sealed. Another difficulty in a process for securing a biologically sealed therapeutic appliance into the wall of the cochlea is safely fenestrating the otic capsule bone without damage to the membranous labyrinth or organ of cord and thus, without damage to hearing.

DISCLOSURE OF INVENTION

An object of the present invention is to facilitate attachment of a microactuator of an implantable hearing aid system or other therapeutic appliance, such as a microactuator, plug or micropump for drug or therapeutic agent delivery, electrodes and the like, to a fenestration formed through a subject's promontory, and to facilitate the therapeutic appliance's subsequent removal.

Another object of the present invention is to attach a microactuator of an implantable hearing aid system or other therapeutic appliance, such as a microactuator, plug or micropump for drug or therapeutic agent delivery, electrodes and the like, to a fenestration formed through the otic capsule bone of a subject's cochlea.

Another object of the present invention is to provide an easily implanted casing for attaching a microactuator of an implantable hearing aid system to a fenestration formed through a subject's promontory.

Yet another object of the present invention is to provide surgical burrs that permit safely fenestrating the otic capsule bone adjacent to the scala tympani of the cochlea without damage to the membranous labyrinth or organ of cord and thus, without damage to hearing.

Briefly, one aspect of the present invention relates to securing a therapeutic appliance, such as a microactuator, plug, micropump for drug or therapeutic agent delivery, electrodes, and the like, into a fenestration that pierces the otic capsule bone of the cochlea. The present invention includes several different ways of achieving a "water tight" seal between the otic capsule bone and the therapeutic appliance. The invention includes specific ways of implanting the therapeutic appliance both with and without a sheath lining the wall of the fenestration.

Another aspect of the present invention includes specialized surgical burrs that enable the otologic surgeon to safely fenestrate the otic capsule bone adjacent to the scala tympani of the cochlea without damage to the basilar membrane or organ of cordi. Utilizing the principles of the invention described herein, other areas of the inner ear may be safely fenestrated provided damage to the membranous labyrinth is avoided, e.g., fenestration of the scala vestibuli of cochlea, bony labyrinth of semicircular canals, or walls of the vestibule. The invention disclosed herein might also be adopted for fenestration of oval or round windows of the inner ear.

These and other features, objects and advantages will be understood or apparent to those of ordinary skill in the art from the following detailed description of the preferred embodiment as illustrated in the various drawing figures.

BRIEF DESCRIPTION OF DRAWINGS

FIG. 1 schematically illustrates a fenestration that pierces the promontory of the cochlea having been formed with fenestration burrs which have precise, compound drilling diameters.

FIG. 2 shows a sectioned, prefabricated casing (sleeve) disposed in the fenestration that receives and secures a microactuator.

FIG. 3 shows how the sleeve may be coated on both sides with an elastomeric antibacterial material, thereby providing a very tight compressive seal.

FIG. 4 shows interposition of an O-ring between the sleeve and the microactuator.

FIG. 5 illustrates application of sealing rings of silastic or similar biocompatible material to the sleeve and/or microactuator.

FIG. 6 shows a plug with an expandable bladder for fixation.

FIG. 7 schematically illustrates how the sleeve may be used with a fully elastomeric plug for delivering a therapeutic agent into the cochlea.

FIG. 8 schematically illustrates how the sleeve may be used with an elastomeric plug and a cochlear electrode implant cable.

FIG. 9 illustrates a elastomeric plug with protruding ring.

FIGS. 10 and 11 schematically illustrate elastomeric plugs inserted into a fenestration and lacking any sleeve.

FIGS. 12a and 12b illustrate fenestration burrs.

FIG. 13 shows a grooved fenestration for anchoring a microactuator.

FIG. 14a shows one type of drill that may be used to make a groove into the wall of the fenestration.

FIG. 14b shows another type of drill that may be used to make a groove into the wall of the fenestration.

FIG. 15 shows the microactuator having protruding elastomeric rings to fit into the grooves.

FIG. 16 is a cross-sectional view of a sleeve illustrating elastomeric rings applied thereto to fit into the grooves.

FIG. 17 shows locations for frequency maxima along a basil coil located within the cochlea, and displacement of the locations for frequency maxima after treatment of the basilar membrane.

DESCRIPTION OF EXAMPLE EMBODIMENTS

FIG. 1 depicts a promontory wall 32 of a cochlea 34 that, in accordance with the present invention, is pierced by a fenestration 36. An upper portion of a bony labyrinth within the cochlea 34 is called the scala vestibuli 42, while a lower portion of the bony labyrinth is called the scala tympani 44. A membranous labyrinth within the cochlea 34, called the scala media 46, lies between the scala vestibuli 42 and scala tympani 44. A "vestibular membrane," called Reissner's membrane 48, separates the scala media 46 from the scala vestibuli 42, while a basilar membrane 52 separates the scala media 46 from the scala tympani 44. A stria vascularis 54 and spiral ligament 56 are juxtaposed with an inner surface of the promontory wall 32.

FIG. 1 also illustrates how precise location of the fenestration 36 may advantageously position a microactuator with great precision in the cochlea 34. Preferably, the cylindrically-shaped fenestration 36 includes two precision sections, an outer section 62 having a larger diameter, and an inner section 64 having a diameter that is smaller than that of the outer section 62. The outer section 62 of the fenestration 36 may be called a well 66. The fenestration 36 includes an annularly-shaped well floor 68 which spans between one edge of the outer section 62 and one edge of the inner section 64. Configured in this way, the fenestration 36 provides a space such that a microactuator may be introduced into the scala tympani 44 for stimulating the basilar membrane 52.

As illustrated in FIG. 2, after the fenestration 36 has been formed through the promontory wall 32 a unitary, i.e. one piece, sleeve 72 may be inserted and fixed firmly within the promontory wall 32 of the cochlea 34. Generally it is desirable that over time the sleeve 72 attach itself permanently to the promontory wall 32. The sleeve 72 may be slit to ease introduction into the fenestration 36, but it should fit tightly after being inserted. The sleeve 72 is preferably made out of very thin titanium e.g. a few mils thick (1 to 10 mils), although elastomeric sleeves may also be used. As described in the '601 patent, the sleeve 72 also preferably includes pre-located keyways 74 for receiving corresponding keys 76 that extend from a microactuator 78. The sleeve 72 with its keyways 74 and the keys 76 permit locking the microactuator 78 in place by inserting the microactuator 78 into the titanium sleeve 72 and rotating it 10° with a very small twist or snap action. Thus, the sleeve 72 precisely locates of the microactuator 78 both laterally and transversely. In this way the microactuator 78 attaches to the sleeve 72 by a method similar to locking a cap on a childproof prescription bottle.

Complete hermetic sealing of the sleeve 72 and the microactuator 78 to the promontory wall 32 is usually accomplished by the body itself. The endothelial lining of the inner ear and the mucosal lining of the inner ear will migrate across a biocompatible membrane, sealing the sleeve 72, microactuator 78 and the fenestration 36, similar to what occurs with the prosthesis following stapedectomy (i.e. fenestration of the stapes).

To improve on the physical and biological sealing while this process occurs, as depicted in FIG. 3 a biocompatible elastomeric coating 82 may be applied both on both inside and outside walls of the titanium sleeve 72. The coatings 82 act as a washer that improves the sealing and fit when the microactuator 78 is inserted into the sleeve 72. The coatings 82 may be impregnated with an antibacterial agent, to imbue the sleeve 72 with prophylactic properties.

Alternatively, as depicted in FIG. 4 an O-ring 84 may be interposed between a floor wall 86 of the sleeve 72 and a shelf 87 of the microactuator 78 to provide a totally leak free seal. The coating 82 may still be applied to the outside of the sleeve 72 to provide a tight seal with the surrounding promontory wall 32. Similar to the coating 82, the O-ring 84 may likewise be impregnated with a prophylactic compound.

FIG. 5 depicts applying a ring 88 of silastic, Teflon, polyethylene, a material which expands upon hydration, or similar biocompatible material along the floor wall 86 of the titanium sleeve 72 and/or the shelf 87 of the microactuator 78. The rings 88 provide a "water tight" seal between the microactuator 78 and the sleeve 72, and also to act as a "spring" to allow compression and rotation of the microactuator 78 as it is "locked" and thus held in place within the sleeve 72.

Alternatively, a pneumatically or hydraulically expandable bladder 91, surrounding either the sleeve 72 or the microactuator 78 or both, may be used for sealing the microactuator 78 within the promontory wall 32. As depicted in FIG. 6, expanding the bladder 91, either pneumatically or hydraulically, tightly seals the microactuator 78 to sleeve 72.

The system described thus far consists of a metal sleeve, accepting a metal body which attaches securely and positively to the former. This fenestration 36 and the sleeve 72 secured therein locate the microactuator 78 precisely in the cochlea 34. Alternatively, it is possible to replace the metal body of the microactuator 78 with a plug made from a soft material that fits in the sleeve 72, and which may be held there by elastic pressure. Under these conditions, the sleeve 72 still provides good lateral positioning for the plug, and can also still provide good transverse location, such that the plug does not penetrate further into the cochlea 34 than desired. Such a soft plug may often be desired when the insert is only temporary, e.g. if the plug is used for delivering a therapeutic agent into the cochlea 34.

In another application for the titanium sleeve 72, a micropump can be securely attached to the titanium sleeve 72 in the fenestration 36 to deliver precisely measured doses of medication directly into the inner ear. This drug delivery system may be shaped similar to the microactuator 78, and enclose a therapeutic agent reservoir right at this location (i.e. for very small volume delivery). The micropump could contain the necessary reservoir of medication when only tiny amounts (microliters) will be delivered from a pulsed piezo-electric mechanism at intervals.

If a larger reservoir of medication is required, a hermetically sealed container made from biocompatible materials (e.g., titanium) may be implanted in the mastoid cavity or subcutaneously. The reservoir is connected to the implanted micropump by hollow tubing extending from the mastoid cavity through the facial recess to a dispensing plug located in the sleeve 72 at the cochlea 34. The micropump is connected to a programmable signal processor and battery implanted either in the mastoid cavity or subcutaneously with leads extending through the facial recess or antrum. The micropump would be activated by telemetry either for single dose or by signal processor programmed by telemetry to adjust the dosage and frequency of medication delivery to the inner ear. The subcutaneous reservoir may be periodically refilled by transcutaneous injection utilizing sterile techniques.

For example, if the drug reservoir is located away from the inner ear, a capillary connection may be made directly to a plug. In the illustration of FIG. 7, the titanium sleeve 72 holds a soft elastomeric plug 92 which receives one end of a capillary 94. The other end of the capillary 94 connects to a reservoir 96 that holds a therapeutic agent. The soft plug 92 itself may contain prophylactic agents, for example to guard against infection.

FIG. 8 depicts this same approach as applied for introducing a cochlear implant electrode cable 102 into the cochlea 34. The cochlear implant electrode cable 102 passes through a hole 104 in the elastomeric plug 92. When disposed within the cochlea 34, the cochlear implant electrode cable 102 is free to move until the plug 92 is pressed into place in the sleeve 72. Upon pressing the plug 92 into the sleeve 72, the hole 104 closes around and circumferentially clamps the cochlear implant electrode cable 102. Though not illustrated in FIG. 8, the soft plug 92 may be tapered or double tapered to provide a good friction fit to the sleeve 72. Hence the structure schematically illustrated in FIG. 8 provides a leak-tight, bacteria-free seal.

As illustrated in FIG. 9, to provide safe anchoring of the soft plug 92, it may be encircled by a raised ring 112 that is adapted to fit into a corresponding outwardly projecting groove 114 that encircles the sleeve 72. Radial compression of the plug 92 upon insertion into the sleeve 72 squeezes the hole 104 to thereby fix any object passing therethrough such as the capillary 94 or the cochlear implant electrode cable 102 which was free to move for adjustment before insertion of the soft plug 92. Even a hard plug 92 may also be attached this way to the sleeve 72.

Finally, FIGS. 10 and 11 illustrate that, for some applications, it is also possible to omit the sleeve 72 altogether; i.e. no sleeve 72 is present. Those elements depicted in FIGS. 10 and 11 that are common to the structures illustrated in FIGS. 1-9 carry the same reference numeral distinguished by a prime ("'") designation. In FIG. 10, the compressive biocompatible elastic plug 92', used with a remote drug delivery system having a reservoir 96', is simply squeezed into the fenestration 36' that pierces the promontory wall 32'. FIG. 11 shows a similar plug 92' used with a cochlear implant electrode cable 102', forced with the plug 92' against the fenestrated promontory wall 32'. As stated previously, the plug 92' depicted in FIGS. 10 and 11 may contain antibacterial compounds for prophylactic action. In either instance illustrated by FIGS. 10 and 11, an expanding re-entrant bladder may be used to provide another way of clamping the plug 92'. Note that the system can again be designed such that the compression upon insertion will fix the cochlear implant electrode cable 102', which is free to move until the plug 92' is inserted into the promontory wall 32'.

Forming the fenestration 36 into the promontory wall 32 of the cochlea 34 or other area of the otic capsule bone as depicted in FIG. 1 is safely performed with guarded fenestration burrs 122 and 124 depicted respectively in FIGS. 12a and 12b. The unitary, i.e. one piece, fenestration burrs 122 and 124 of the present invention permit forming a precise 1.4 mm diameter inner section 64 of the fenestration 36 and a 1.8 mm diameter well 66 in the promontory wall 32 of the cochlea 34 as illustrated in FIG. 1. The fenestration burrs 122 and 124 respectively attach to a conventional, low frequency microdrill (<2000 rpm), e.g. Synergy stapes hand piece, for rotating the fenestration burrs 122 and 124 during formation of the fenestration 36. Since the microdrill is conventional, it is not illustrated in any of the figures. An elongated shaft 128 of each of the fenestration burrs 122 and 124, with respect to which all diameters specified below for the fenestration burrs 122 and 124 are measured, can be readily adapted for use with any selected one of several commercially available ear microdrills. The fenestration burrs 122 and 124 are guarded to limit penetration into scala tympani 44 and thus, avoid injury to the structures of cochlea 34 illustrated in FIG. 1. Flutes on the fenestration burrs 122 and 124 are configured to discharge bone dust away from the cochlea.

The initial fenestration burr 122 illustrated in FIG. 12a has dimensions that are based on the thickness of the promontory wall 32 at the proposed fenestration site measured in 12 human cochleae. The initial fenestration burr 122 includes a cutting burr 132 that is 1.4 mm in diameter and is located at a distal end of the shaft 128 furthest from the microdrill. A second, cylindrically-shaped polishing burr 134 is located along the shaft 128 near, e.g. 0.5 mm, from the cutting burr 132 and formed concentrically on the shaft 128 with the cutting burr 132. The polishing burr 134 is diamond studded, is 1.8 mm in diameter and extends 0.5 mm along the shaft 128 from a washer-shaped flange or collar 136 that is formed concentrically on the shaft 128 with the cutting burr 132 and the polishing burr 134. During use, the polishing burr 134 drills a 0.5 mm deep well 66, i.e. the outer section 62, in the promontory wall 32 of the cochlea 34 while the cutting burr 132 begins forming the smaller diameter inner section 64 of the fenestration 36. The collar 136, which is 2.0 mm in diameter and is juxtaposed with a side of the polishing burr 134 furthest from the cutting burr 132, contacts an outer surface of the promontory wall 32 to limit penetration of the initial fenestration burr 122 thereinto.

A sequence of five (5) subsequent fenestration polishing burrs 124, illustrated by the fenestration polishing burr 124 in FIG. 12b, are used to complete penetration of the promontory wall 32 and formation of the inner section 64 of the fenestration 36. Each of the fenestration polishing burrs 124 includes a polishing burr 142 that is 1.4 mm in diameter. The each of fenestration polishing burrs 124 also includes a protective washer-shaped collar 146 that is located a short distance from the polishing burr 142 as indicated by an arrow 144 in FIG. 12b, and formed concentrically on the shaft 128 with the polishing burr 142. The distal end of the polishing burrs 142 in the sequence of fenestration polishing burrs 124 respectively extend a distance further and further from the collar 146. Preferably the distal end of polishing burr 142 in the sequence of fenestration polishing burrs 124 extends respectively 0.75 mm, 1.00 mm, 1.25 mm, 1.50 mm and 1.75 mm from the collar 146. The collar 146 measures 1.8 mm diameter and reaches to a well floor 68 of the well 66, thus centering the polishing burr 142 as well as limiting its penetration.

A microactuator, micropump, electrode or similar device may be attached in the following way to the fenestration 36 in the promontory wall 32 of the cochlea 34 or other area of the otic capsule without the sleeve 72 lining the fenestration 36. First the fenestration 36 is safely formed in the promontory wall 32 of the cochlea 34 or other area of the otic capsule using the guarded fenestration burrs 122 and 124 depicted in FIGS. 12a and 12b and described above. Next, as depicted in FIG. 13, circumferential grooves 152 and 154 (e.g. 0.10-0.15 mm in depth) are drilled into the bony wall surrounding the fenestration 36 respectively encircling the outer section 62 and the inner section 64 at precise distances respectively below and above the well floor 68 of the well 66. In certain instances a single groove 152 or 154 may be sufficient for the intended purpose. The grooves 152 and 154 can be precisely formed as described below using fenestration grooving burrs 162 and 164 depicted respectively in FIGS. 14a and 14b.

Each of the unitary, i.e. one piece, fenestration grooving burrs 162 and 164 includes an elongated shaft 166 similar to the shaft 128 of the fenestration burrs 122 and 124 depicted respectively in FIGS. 12a and 12b. Similar to the fenestration burrs 122 and 124, the fenestration grooving burrs 162 and 164 also respectively attach to a conventional, low frequency microdrill (<2000 rpm) that is not illustrated in any of the figures. Each of the fenestration grooving burrs 162 and 164 also includes a washer-shaped collar 168. Each collar 168 is slightly larger than the diameter of the inner section 64 of the fenestration 36 depicted in FIG. 1 (e.g. 1.5 mm diameter), but smaller than the diameter of the well 66. Such a diameter for the collar 168 permits resting the collar 168 on the well floor 68 of the well 66 when drilling the groove 152 or 154, but allowing movement of the fenestration grooving burr 162 or 165 laterally, eccentrically 360° around the circumference of the fenestration during drilling.

The fenestration grooving burr 162 depicted in FIG. 14a also includes a cutting wheel 172 that is located at a distal end of the shaft 166 a short distance from the collar 168 and formed concentrically on the shaft 166 with the collar 168. If the inner section 64 has a diameter of 1.4 mm, the well 66 has a diameter of 1.8 mm and the collar 168 has a diameter of 1.4 mm, a 1.4 mm diameter for the cutting wheel 172 permits drilling 0.15 mm deep groove 154 circumferentially in the inner section 64 of the fenestration 36 at a precise distance below the well floor 68 of the well 66. The depth of the groove 154 drilled by the fenestration grooving burr 162 is controlled by the difference in diameters between the collar 168 and the cutting wheel 172, and between the inner section 64 and the well 66.

The fenestration grooving burr 164 depicted in FIG. 14b includes the collar 168 that is located at a distal end of the shaft 166 and a cutting wheel 176 that is located along the shaft 166 a short distance from collar 168 and formed concentrically on the shaft 166 with the collar 168. The fenestration grooving burr 164 can be used to make the groove 152 above the well 66 of the well 66. Again, during formation of the groove 152 the collar 168 rests on the well 66 of the well 66. If the well 66 has a diameter of 1.8 mm and the collar 168 a diameter of 1.5 mm, a 1.8 mm diameter for the cutting wheel 176, i.e. equal to the diameter of the well 66, produces a 0.15 mm deep groove 152 in the promontory wall 32 surrounding the well 66 a precise distance above the well floor 68 of the well 66.

Installation of the microactuator 78, micropump or cochlear implant electrode cable 102, etc. into the fenestration 36 depicted in FIG. 13 can be stabilized in the following way. As depicted in FIG. 15, one or more rings 182 and 184 of pliable material are permanently attached around the microactuator 78 at appropriate locations along the microactuator 78. Upon inserting the microactuator 78 into the fenestration 36 depicted in FIG. 13, the rings 182 and 184 compress and then expand into the corresponding grooves 152 and 154 as the microactuator 78 reaches the proper depth thereby fixing the microactuator 78 in the grooves 152 and 154. Similar to the ring 88 depicted in FIG. 5, several different biocompatible materials may be used for the rings 182 and 184, including silastic, Teflon, polyethylene, a material which expands upon hydration, or similar biocompatible material. As described above, this method for attaching the microactuator 78 to the grooved fenestration 36 avoids any need for the sleeve 72 to line the fenestration 36. Similar to the coating 82 depicted in FIG. 3 and the O-ring 84 depicted in FIG. 4, if beneficial the rings 182 and 184 may be impregnated with prophylactic material.

A ring 186 of pliable biocompatible material may also be applied around the distal end of the microactuator 78 or other device to expand upon reaching the lumen of the cochlea 34, e.g. scala tympani 44 or scala vestibuli 42. Use of the ring 186 may avoid any need for grooving the wall of the fenestration 36, but requires that the fenestration 36 have a precise, pre-established depth.

As best illustrated in FIG. 15, the microactuator 78 includes an outer barrel 192 which abuts the annularly-shaped shelf 87 along a circular common edge 194. During implantation of the microactuator 78 directly into the fenestration 36, the outer barrel 192 is inserted into and becomes fixed firmly in the outer section 62, and the shelf 87 to be juxtaposed with the well floor 68 of the fenestration 36. The microactuator 78 also includes an inner barrel 196 which projects away from the outer barrel 192 and abuts the common edge 194 along a circular common edge 198. During implantation of the microactuator 78 directly into the fenestration 36, the inner barrel 196 is inserted into and becomes fixed firmly into the inner section 64.

As depicted in FIG. 16, in those instances in which the sleeve 72 is desired so the microactuator 78 or other device may be easily removed, the rings 182 and 184 and/or ring 186 are applied abound the sleeve 72 rather than the microactuator 78 so the sleeve 72 may be inserted and held in place within the fenestration 36 similar to the microactuator 78 depicted in FIG. 15. As depicted in FIG. 16, a thin layer 202 of silastic, Teflon, polyethylene, a material which expands upon hydration, or similar biocompatible material may also be applied to coat the floor wall 86 of the sleeve 72, and/or an optional flange 204 that is located at the top of the titanium sleeve 72. The thin layers 202 provide a water tight seal between the microactuator 78 or other device and the sleeve 72, and also act as a spring that allows compression and motion of the microactuator 78 as it is locked and then held in place within the sleeve 72. Similar methods may be used for fixing a micropump, electrode, or combination microactuator and electrode in the fenestration 36.

As best illustrated in FIGS. 16 and 2, the sleeve 72 includes an outer wall 212 which abuts the annularly-shaped floor wall 86 along a circular common edge 214. During implantation of the sleeve 72 into the fenestration 36, the outer wall 212 is inserted into and becomes fixed firmly in the outer section 62, and the floor wall 86 becomes juxtaposed with the well floor 68 of the fenestration 36. The sleeve 72 also includes an inner wall 216 which projects away from the outer wall 212 and abuts the common edge 214 along a circular common edge 218. During implantation of the sleeve 72 into the fenestration 36, the inner wall 216 is inserted into and becomes fixed firmly into the inner section 64. Implantation of the microactuator 78 into the sleeve 72 causes the outer barrel 192 to be inserted into and fixed firmly in the outer wall 212, and the shelf 87 to be juxtaposed with the floor wall 86 of the sleeve 72. Correspondingly, implantation of the microactuator 78 into the sleeve 72 also causes the inner barrel 196 to be inserted into a fixed firmly into the inner wall 216.

The most common type of sensorineural hearing loss is decreased sensitivity to high frequency sound caused by aging, noise exposure, diabetes, oto-toxicity, impaired blood supply to the inner ear, etc. High frequency hearing loss results from a deterioration of hair cells in a basal coil 222 of the cochlea 34. Because of the complicated nature of hair-cells, they do not regenerate.

The cochlea 34 acts as a frequency analyzer, with the traveling wave reaching a maximum at various locations along the basilar membrane 52. The high frequency maxima occur in the basal coil 222 of the cochlea 34 near the stapes, and the low frequency maxima near the apex due to the stiffness gradient of the basilar membrane 52. This separation of maxima along the basal coil 222 is schematically illustrated in FIG. 17, which shows the location of the various frequency maxima along the basilar membrane 52.

If a therapeutic agent or procedure is introduced into the cochlea 34 such that the basilar membrane 52 is made stiffer or its motion in the basal coil 222 of the cochlea 34 blocked, the traveling wave of basilar membrane displacement will move towards the apex of the cochlea 34 depicted in FIG. 17. For example, the location of maximum displacement for 10 kHz sound could be moved along the basal coil 222 to the location that previously sensed 2 kHz sound, the location of maximum displacement for 5 kHz might be moved to the area previously stimulated by 1 kHz etc.

If the basal coil 222 of scala media 46 has no viable hair cells from its most proximal point near the round window to the mid turn of the basal coil 222, then the basal coil 222 would not produce nerve impulses for high frequencies, e.g. 10 kHz through 4 kHz, and thus would be insensitive ("deaf") to these frequencies. Movement of the traveling wave apically (i.e. towards the apex) along the basilar membrane 52 to a location where hair cells are still present would now permit depolarization of those hair cells thereby converting the sound into nerve impulses. In this way intact haircells are all used to the maximum extent possible to cover the entire frequency range.

Computer simulation studies and mechanical models of the cochlea 34 indicate that if the traveling wave is moved apically the wave envelope is compressed but still the "phase/time" analysis performed by the traveling wave is maintained in this compressed state. Clinical studies from electrical stimulation of the cochlea 34 with cochlear implants confirm that the brain can be retrained to interpret these new auditory messages, and speech discrimination is possible. In essence, by moving the traveling wave apically in a subject who has no surviving hair cells in the basal coil 222 permits stimulating the remaining hair cells with high frequencies thereby allowing them to "volley" in synchrony with the high frequencies. Neuro-physiologic studies confirm that hair cells throughout the cochlea 34 have similar depolarization/repolarization characteristics and thus theoretically are capable of synchronous depolarization at frequencies from 100 to 20 kHz throughout the cochlea 34.

Hearing sensitivity of the cochlea 34 is measured by pure tone threshold bone conduction audiometric studies, which stimulate the fluid within the cochlea 34 directly. High frequency nerve loss implies a loss of hair cells in the basal coil 222 of the cochlea 34. Because the location of frequency maxima along the basilar membrane 52 is well known, the amount of transposition of the traveling wave to areas where hair cells are intact can be determined by bone conduction audiometry. The treatment of the basilar membrane 52 would then be adapted so that the required basilar membrane stiffening or restriction of its motion is affected to that degree required for correctly projecting sound at specific frequencies onto the remaining part of the basal membrane which has intact hair cells.

Stiffening the basilar membrane 52 could be accomplished with a therapeutic agent such as a drug, a cell regrowth factor, or any factor that reduces or stiffens the elasticity of the basilar membrane 52. An alternative method is to obstruct the motion of the basilar membrane 52 in the scala tympani 44 by physically limiting its downward motion with a bio-compatible material which would completely obstruct scala tympani 44 in the basal coil 222 to the desired length of the cochlea 34. This would require creating a new round window in the scala tympani distal to the point of obstruction if sound vibrations are to enter the cochlea 34 through the oval window. Conversely, a microactuator could be attached to the distal end of the material obstructing the scala tympani 44, and sound introduced directly into scala tympani 44. In this scenario, the oval window would provide the necessary hydraulic decompression to permit the traveling wave of pressure and displacement without significantly increasing fluid impedance. It is recognized because of the impedance mismatching of the basilar membrane 52 that greater energy will be necessary to displace the basilar membrane 52 with this obstructing technique. Again the traveling wave envelope will be compressed in both the horizontal and vertical planes.

INDUSTRIAL APPLICABILITY

In general, many if not all of the methods depicted in FIGS. 3 through 11 and described above can be used when attaching a microactuator, a micropump, capillary, electrode, or combination microactuator/electrode into a fenestration 36 that pierces the wall of the cochlea 34.

Using structures such as those depicted in FIGS. 7 and 10, it is anticipated that conditions such as vertigo, tinnitus, sudden sensorineural hearing loss, endolymphatic hydrops (Meniere's disease), autoimmune inner ear disease, and serous or viral labyrinthitis could be improved by carefully perfusing measured doses of a variety of medications (e.g. steroids, a medication to suppress tinnitus, a medication to alter electrolyte balance in perilymph or endolymph, vasodilators, immune suppressants, anticoagulants, antibiotics, antiviral agents, plasma expanders, antioxidants, etc.) directly into the inner ear. Research has recently discovered that hair cells in the cochlea 34 and vestibular labyrinth of some vertebrates have the ability to regenerate. The micropump can perfuse a substance (e.g., neurohormone, hair cell DNA actuator, Math1 or other gene therapy to enhance hair cell growth factor to encourage efferent nerve growth) into the inner ear to stimulate regrowth of hair cells in the cochlea 34 in patients with sensorineural hearing loss or repair damaged vestibular hair cells.

Another use for this invention depicted in FIGS. 8 and 11 is introducing an electrode into the inner ear and securely attaching it to the bony walls of the promontory wall 32. In addition to fixing the cochlear implant electrode cable 102 into the cochlea 34, application of low dose electrical current can depolarize hair cells or neurons and may someday be used to relieve tinnitus or vertigo triggered by irritable peripheral hair cells or afferent neurons.

In each of the applications described above, attaching the microactuator, micropump, or electrode to the titanium sleeve 72 lining the fenestration 36 enables the surgeon to remove the device with minimal risk of damage to the inner ear. A new device can be inserted to replace an existing one, or an existing device may be replaced by a "plug" if the device is no longer needed.

Although the present invention has been described in terms of the presently preferred embodiment, it is to be understood that such disclosure is purely illustrative and is not to be interpreted as limiting. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as encompassing all alterations, modifications, or alternative applications as fall within the true spirit and scope of the invention.

What is claimed is:

1. A therapeutic appliance configured for insertion into a cylindrically-shaped fenestration that pierces a wall of a cochlea of a subject, the therapeutic appliance comprising:
   a cylindrically shaped outer barrel having an outer cylindrical surface configured to be disposed at a distal end of the wall of the cochlea and configured to be inserted into and firmly fixed in a corresponding outer portion of the cylindrically-shaped fenestration, the outer barrel having an outer diameter dimension along a longitudinal axis, the outer surface of the outer barrel configured to be in contact with the distal end of the fenestration in the wall of the cochlea; and
   a cylindrically shaped inner barrel having an outer cylindrical surface configured to be disposed at a proximal end of the wall of the cochlea closest to the scala tympani region of the cochlea and opposite to the distal end, the inner barrel coupled to the outer barrel and extending away from the outer barrel along the longitudinal axis toward the proximal end, the inner barrel having an inner barrel diameter dimension about the longitudinal axis, wherein the inner barrel diameter dimension is smaller than the outer barrel diameter dimension, the inner barrel configured to be inserted into and to be firmly fixed in a corresponding inner portion of the fenestration adjacent to the outer portion of the fenestration, the outer surface of the inner barrel configured to be in contact with the proximal end of the fenestration in the wall of the cochlea, wherein a sleeve is positioned between the fenestration and the therapeutic appliance such that the inner barrel is in contact with a first circular area of the sleeve having a first sleeve diameter dimension corresponding to the inner barrel diameter dimension and the outer barrel is in contact with a second circular area of the sleeve having a second sleeve diameter dimension corresponding with the outer barrel diameter dimension.

2. The therapeutic appliance of claim 1, further comprising:
   an annularly-shaped shelf positioned between the inner barrel and the outer barrel, the shelf having a shelf diameter dimension less than the outer barrel diameter dimension and greater than the inner barrel diameter dimension.

3. The therapeutic appliance of claim 1, further comprising:
   a biocompatible elastomeric coating disposed on an outer surface of the therapeutic appliance, the coating for effecting a seal between the outer surface of the therapeutic appliance and the sleeve.

4. The therapeutic appliance of claim 1, further comprising:
   an expandable bladder configured to be interposed between the therapeutic appliance and the sleeve for effecting a seal therebetween.

5. The therapeutic appliance of claim 1, wherein the outer barrel of the therapeutic appliance is encircled by at least one ring that is configured to mate with and engage a corresponding groove of the sleeve.

6. The therapeutic appliance of claim 1, wherein the inner barrel of the therapeutic appliance is encircled by at least one ring that is configured to mate with and engage a corresponding groove of the sleeve.

7. The therapeutic appliance of claim 2, further comprising:
   an O-ring disposed on an outer surface of the shelf of the therapeutic appliance for effecting a seal between the sleeve and the shelf.

8. A therapeutic appliance configured to be implanted into a correspondingly shaped fenestration in a wall of a cochlea, the therapeutic appliance comprising:
   a cylindrically shaped outer barrel having an outer cylindrical surface configured to be disposed distally from an inner section of the cochlea, the outer barrel having an outer barrel diameter dimension along a longitudinal axis, the outer surface of the outer barrel configured to be in contact with the distal end of the fenestration in the wall of the cochlea; and
   a cylindrically shaped inner barrel having an outer cylindrical surface configured to be disposed proximally to the inner section of the cochlea in communication with the scala tympani region of the cochlea, the inner barrel aligned coaxial with and adjacent to the outer barrel along the longitudinal axis such that the inner barrel extends away from the outer barrel, the inner barrel having an inner barrel diameter dimension about the longitudinal axis, wherein the inner barrel diameter dimension is smaller than the outer barrel diameter dimension, the outer surface of the inner barrel configured to be in contact with the proximal end of the fenestration in the wall of the cochlea and further comprising:
   a shelf positioned between the inner and outer barrels having a length dimension along the longitudinal axis, the shelf having a shelf diameter dimension, wherein the shelf diameter dimension is smaller than the outer barrel diameter dimension and larger than the inner barrel diameter dimension.

* * * * *